(12) United States Patent
Fischell et al.

(10) Patent No.: US 7,107,096 B2
(45) Date of Patent: Sep. 12, 2006

(54) SYSTEM FOR PATIENT ALERTING ASSOCIATED WITH A CARDIAC EVENT

(75) Inventors: David R. Fischell, Fair Haven, NJ (US); Jonathan Harwood, Rumson, NJ (US); Mary Carol Day, Middletown, NY (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 73 days.

(21) Appl. No.: 10/765,040

(22) Filed: Jan. 28, 2004

(65) Prior Publication Data

US 2005/0165321 A1    Jul. 28, 2005

(51) Int. Cl.
  *A61B 5/00*      (2006.01)
(52) U.S. Cl. ............... 600/515; 600/508; 600/509
(58) Field of Classification Search ........ 600/515–518, 600/523, 525, 508, 509
  See application file for complete search history.

(56) References Cited

U.S. PATENT DOCUMENTS

| | | | |
|---|---|---|---|
| 5,076,272 A | * | 12/1991 | Ferek-Petric ............ 607/28 |
| 6,067,473 A | * | 5/2000 | Greeninger et al. .......... 607/32 |
| 6,095,984 A | * | 8/2000 | Amano et al. .............. 600/500 |
| 6,112,116 A | | 8/2000 | Fischell et al. |
| 6,171,237 B1 | * | 1/2001 | Avitall et al. ............... 600/300 |
| 6,230,049 B1 | | 5/2001 | Fischell et al. |
| 6,272,379 B1 | * | 8/2001 | Fischell et al. ................ 607/5 |
| 6,571,128 B1 | * | 5/2003 | Lebel et al. .................. 607/60 |
| 6,609,023 B1 | * | 8/2003 | Fischell et al. ............ 600/515 |
| 2003/0050566 A1 | * | 3/2003 | Ujhelyi et al. ............. 600/515 |
| 2003/0191403 A1 | * | 10/2003 | Zhou et al. ................. 600/515 |
| 2003/0204209 A1 | * | 10/2003 | Burnes et al. ................ 607/14 |

* cited by examiner

*Primary Examiner*—Robert Pezzuto
*Assistant Examiner*—Shevon Johnson
(74) *Attorney, Agent, or Firm*—Rosenberg, Klein & Lee

(57) ABSTRACT

A system for the detection of cardiac events occurring in a human patient is provided. At least two electrodes are included in the system for obtaining an electrical signal from a patient's heart. An electrical signal processor is electrically coupled to the electrodes for processing the electrical signal and a patient alarm is further provided and electrically coupled to the electrical signal processor. The patient alarm generates an escalating sensory alarm signal over a predetermined time period subsequent to the electrical signal processor if the processor detects a cardiac event. The patient alarm may be further applied to a pacemaker or defibrillator system.

34 Claims, 6 Drawing Sheets

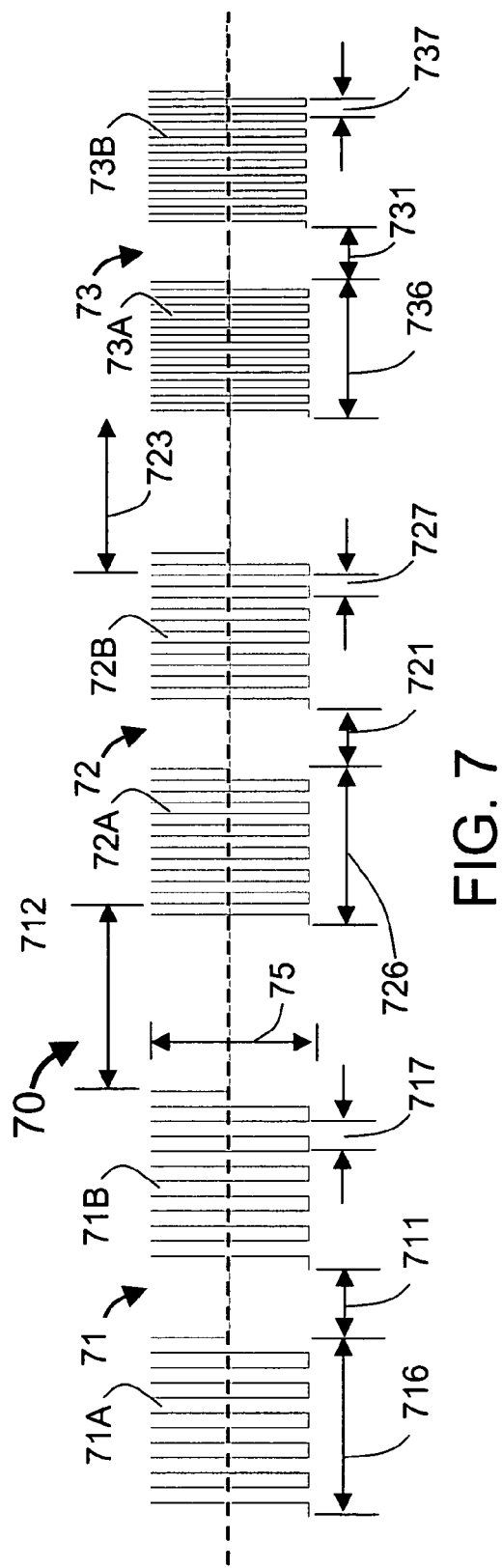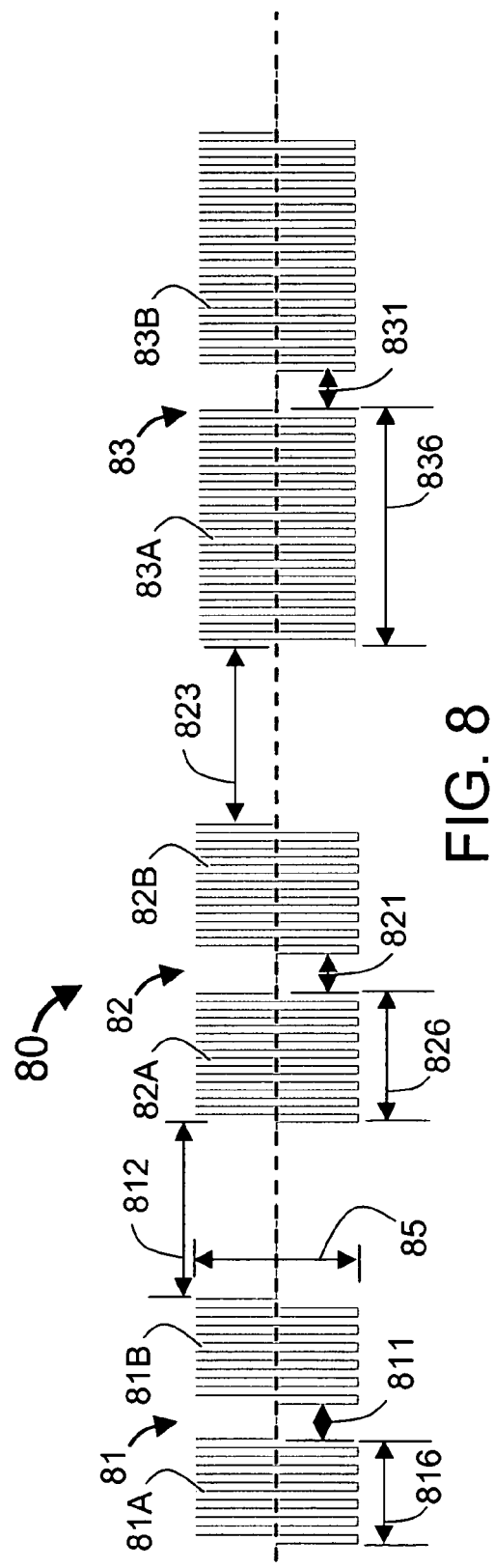

SYSTEM FOR PATIENT ALERTING ASSOCIATED WITH A CARDIAC EVENT

FIELD OF USE

This invention is in the field of implantable medical device systems that monitor a patient's cardiovascular condition.

BACKGROUND OF THE INVENTION

Heart disease is the leading cause of death in the United States. A heart attack (also known as an acute myocardial infarction (AMI)) typically results from a thrombus (i.e., a blood clot) that obstructs blood flow in one or more coronary arteries. AMI is a common and life-threatening complication of coronary artery disease. Coronary ischemia is caused by an insufficiency of oxygen to the heart muscle. Ischemia is typically provoked by physical activity or other causes of increased heart rate when one or more of the coronary arteries is narrowed by atherosclerosis. AMI, which is typically the result of a completely blocked coronary artery, is the most extreme form of ischemia. Patients will often (but not always) experience chest discomfort (angina) when the heart muscle is experiencing ischemia. Those with coronary atherosclerosis are at higher risk for AMI if the plaque becomes further obstructed by thrombus.

The current treatment for a coronary artery narrowing (a stenosis) is the insertion of a drug-eluting stent such as the Cypher™ sirolimus-eluting stent from Cordis Corporation or the Taxus™ paclitaxel-eluting stent from the Boston Scientific Corporation. The insertion of a stent into a stenosed coronary artery is a reliable medical treatment to eliminate or reduce coronary ischemia and to prevent the complete blockage of a coronary artery, which blockage can result in an AMI.

Acute myocardial infarction and ischemia may be detected from a patient's electrocardiogram (ECG) by noting an ST segment shift (i.e., voltage change). However, without knowing the patient's normal ECG pattern, detection from a standard 12 lead ECG can be unreliable.

Fischell et al. in U.S. Pat. Nos. 6,112,116, 6,272,379 and 6,609,023 describe implantable systems and algorithms for detecting the onset of acute myocardial infarction and providing both patient alerting and treatment. The Fischell et al. patents describe how the electrical signal from inside the heart (which is called an "electrogram") can be used to determine various states of myocardial ischemia.

The Reveal™ subcutaneous loop Holter monitor sold by Medtronic, Inc., uses two case electrodes spaced about 3 inches apart to record electrocardiogram information. Recording can be triggered automatically when arrhythmias are detected or upon patient initiation using an external device. The Reveal is designed to record electrogram data only and does not include a patient alerting capability. The Reveal also does not have the capability to measure or alert the patient if there is an ST segment shift. In fact, the Reveal's high pass filtering and electrode spacing preclude accurate detection of changes in the low frequency aspects of the heart's electrical signal such as the ST segment of the electrogram.

While pacemakers and Implantable Cardioverter Defibrillators (ICDs) monitor the patient's electrogram, they do not currently detect ST segment changes nor provide patient alerting.

The term "medical practitioner" shall be used herein to mean any person who might be involved in the medical treatment of a patient. Such a medical practitioner would include, but is not limited to, a medical doctor (e.g., a general practice physician, an internist or a cardiologist), a medical technician, a paramedic, a nurse or an electrogram analyst. Although the masculine pronouns "he" and "his" are used herein, it should be understood that the patient, physician or medical practitioner could be a man or a woman. A "cardiac event" includes an acute myocardial infarction, ischemia caused by effort (such as exercise) and/or an elevated heart rate, bradycardia, tachycardia or an arrhythmia such as atrial fibrillation, atrial flutter, ventricular fibrillation, and premature ventricular or atrial contractions (PVCs or PACs respectively).

It is generally understood that the term "electrocardiogram" is defined as the heart's electrical signals sensed by means of skin surface electrodes that are placed in a position to indicate the heart's electrical activity (depolarization and repolarization). An electrocardiogram segment refers to a portion of electrocardiogram signal that extends for either a specific length of time, such as 10 seconds, or a specific number of heart beats, such as 10 beats. A beat is defined as a sub-segment of an electrogram or electrocardiogram segment containing exactly one R wave. As used herein, the PQ segment of a patient's electrocardiogram or electrogram is the typically straight segment of a beat of an electrocardiogram or electrogram that occurs just before the R wave and the ST segment is a typically straight segment that occurs just after the R wave.

Although often described as an electrocardiogram (ECG), the electrical signal from the heart as measured from electrodes within the body is properly termed an "electrogram". As defined herein, the term "electrogram" is the heart's electrical signal voltage as sensed from one or more implanted electrode(s) that are placed in a position to indicate the heart's electrical activity (depolarization and repolarization). An electrogram segment refers to a portion of the electrogram signal for either a specific length of time, such as 10 seconds, or a specific number of heart beats, such as 10 beats. For the purposes of this specification, the terms "detection" and "identification" of a cardiac event have the same meaning.

A heart signal parameter is defined to be a measured or calculated value created during the processing of one or more beats of the electrogram (or electrocardiogram). Heart signal parameters include the following: ST deviation (ST segment average value minus PQ segment average value), ST shift (ST deviation compared to a baseline average ST deviation), average signal strength, T wave peak height, T wave average value, T wave deviation, QRS complex width, number of PVCs per unit time, heart rate and R-R interval.

SUMMARY OF THE INVENTION

The present invention system for the detection of coronary ischemia (including AMI) as described herein shall be called the "Guardian" system. The Guardian system detects cardiac events using an implanted sub-system called a "cardiosaver system" which is designed to detect cardiac events including arrhythmias and coronary ischemia. A "cardiac event" can be an acute myocardial infarction, ischemia caused by effort (such as exercise) and/or an elevated heart rate, bradycardia, tachycardia or an arrhythmia such as atrial fibrillation, atrial flutter, ventricular fibrillation, and premature ventricular or atrial contractions (PVCs or PACs respectively). The present invention cardiosaver system is designed to detect ischemia (including AMI) by identifying ST segment changes in a positive direction (ST elevation) or negative direction (ST depression).

The cardiosaver system includes electrodes placed to advantageously sense electrical signals from the heart that is the electrogram. The electrodes can be placed within the heart and/or subcutaneously. The implanted portion of the Guardian system is the cardiosaver system as described by Fischell et al. in U.S. Pat. Nos. 6,112,116, 6,272,379 and 6,609,023, each of these patents being incorporated herein by reference. The Guardian system also includes external equipment that can include a physician's programmer and an external alarm device also described in the Fischell et al. patents.

The present invention is a cardiosaver system that utilizes techniques for patient alerting designed to ensure the patient knows what is happening without startling the patient, which could cause an unwanted rise in heart rate at the time of a cardiac event when it is important to remain calm.

In the Fischell et al. patents mentioned above, the concept of internal and external alarm signals is discussed, including the technique of using different patterns of sound, vibration or electrical tickle to assist the patient in differentiating between an emergency (major or critical) alarm where immediate medical attention is needed and a "see your doctor" alert where an appointment should be scheduled as soon as convenient.

The present invention alerting system improves upon the Fischell et al. concepts by using alert escalation techniques that will communicate the emergency alarm, see doctor alert and/or other patient alert messages without startling or scaring the patient. One embodiment of the present invention uses an increasing amplitude of vibration over time from an internal alarm signal within the implanted cardiosaver. For example, the vibration amplitude might increase over a period of several minutes until it reaches a pre-set level. The escalating amplitude technique can also be applied if the internal alarm uses an electrical tickle or other means of alerting the patient. Also the present invention Guardian system may include an increasing amplitude for the external alarm signal generated by the external alarm system mentioned by Fischell et al. The external alarm signal can be a sound, vibration or visual display with sound being the preferred embodiment.

It is also envisioned that not only can the amplitude of the internal and/or external alarm signals be increased over time, but the pattern and frequency of the signal might change. For example, the internal alarm might use sets of three successive vibrations with a short time between vibrations within a set and a longer time between sets where the time between sets of vibrations might decrease over time. The time between vibrations within a set might also decrease as the alert escalates. Another example might have the external alarm signal using a tone or tone sequence that increases in the pitch of the tones as the alert escalates. Finally, if a visual display using sets of light flashes is used as the external alarm signal, then the escalation might include the brightness of the flashes, an increase in the number of the flashes within a set, a decrease in the time between sets and a change in the color of the flashes.

For the purposes of this invention, the term "alarm signal" refers to the complete signal internally or externally generated to alert the patient to the detection of a cardiac event. An alarm signal will continue until a timer turns it off after a pre-set time period (e.g., 5 minutes) or an alarm silence command is provided to the source generating the alarm. A typical alarm signal will be made up of a sequence of short (less than 10 seconds long) alerting signals. The alerting signals may be produced in sets with an inter-set time interval defined as the time interval between sets of alerting signals and the intra-set time interval defined as the time between alerting signals within a set of alerting signals.

So in summary, the present invention is an implanted system for the detection of cardiac events having any combination of internal alarm signals and external alarm signals where, over the initial period of patient alerting, the alarm signals escalate by any or all of the following:

a) An increase in amplitude of alerting signals over time;
b) An increase in the number of alerting signals per set;
c) A decrease in the time between alerting signals within a set;
d) A decrease in the time between sets of alerting signals;
e) A change in the frequency (vibrational frequency, sound pitch, color) of the alerting signals; and,
f) An increase in the frequency, length and/or amplitude of each alerting signal within a set (including a set of one alerting signal).

Another embodiment of the present invention is an implanted ischemia detection device with patient alerting that also includes pacemaker circuitry to pace the patient's heart as needed. Still another embodiment is an implanted ischemia detection device with patient alerting that includes Implantable Cardiac Defibrillator (ICD) circuitry to defibrillate the patient's heart as needed. Yet another embodiment is an implanted ischemia detection device with patient alerting that includes a combination of pacemaker and ICD circuitry.

It is also envisioned that there could be an escalating pattern where the number of alerting signals in each set increases while the length of each alerting signal decreases.

It is also envisioned that the escalation of alerting might involve the sequencing of internal and external alarms. For example, the external alarm signal might begin first as people who are used to phones ringing are less likely to be startled by external alerting sounds. After a preset period of time, the internal alarm signal might begin. Neither, either or both the external and internal alarm signals in such a sequential activation might use one or more alarm signals that escalate by the means described above.

Thus it is an object of this invention to have a Guardian system that can alert a patient to the detection of a cardiac event without causing a startle response.

Another object of this invention is to have a Guardian system that can alert a patient to the detection of a cardiac event where the alarm signal escalates over time.

Still another object of this invention is to have a Guardian system that can alert a patient to the detection of a cardiac event where the alarm signal escalates by increasing amplitude over time.

Still another object of this invention is to have a Guardian system that can alert a patient to the detection of a cardiac event where the alarm signal escalates by increasing frequency over time.

Yet another object of this invention is to have a Guardian system that can alert a patient to the detection of a cardiac event where the alarm signal escalates by decreasing the time between alerting signals within sets of the alarm signal.

Yet another object of this invention is to have a Guardian system that can alert a patient to the detection of a cardiac event where the alarm signal escalates by decreasing the time between sets of alerting signals within the alarm signal.

Yet another object of this invention is to have a Guardian system that can alert a patient to the detection of a cardiac event where the alarm signal escalates by increasing the number of alerting signals within sets of the alarm signal.

Yet another object of this invention is to have a Guardian system that can alert a patient to the detection of a cardiac event where the alarm signal escalates by increasing the frequency, length and/or amplitude of each alerting signal with a set (including a set of one alerting signal).

Yet another object of the present invention is to have a Guardian system with an implanted component having the capability to generate an internal alarm signal and an external alarm system capable of generating an external alarm signal where the patient alert initiates the external alarm signal before the internal alarm.

Yet another object of the present invention is to have a Guardian system with an implanted component having the capability to generate an internal alarm signal and an external alarm system capable of generating an external alarm signal where the patient alert initiates the internal alarm signal before the external alarm.

These and other objects and advantages of this invention will become obvious to a person of ordinary skill in this art upon reading of the detailed description of this invention including the associated drawings as presented herein.

BRIEF DESCRIPTION OF THE DRAWINGS

FIG. 7 illustrates a change in frequency of alerting signals as the patient alert escalates;

FIG. 8 illustrates a change in the length of each alerting signal within a set of alerting signals as the patient alert escalates;

DETAILED DESCRIPTION OF THE INVENTION

Figure 1:
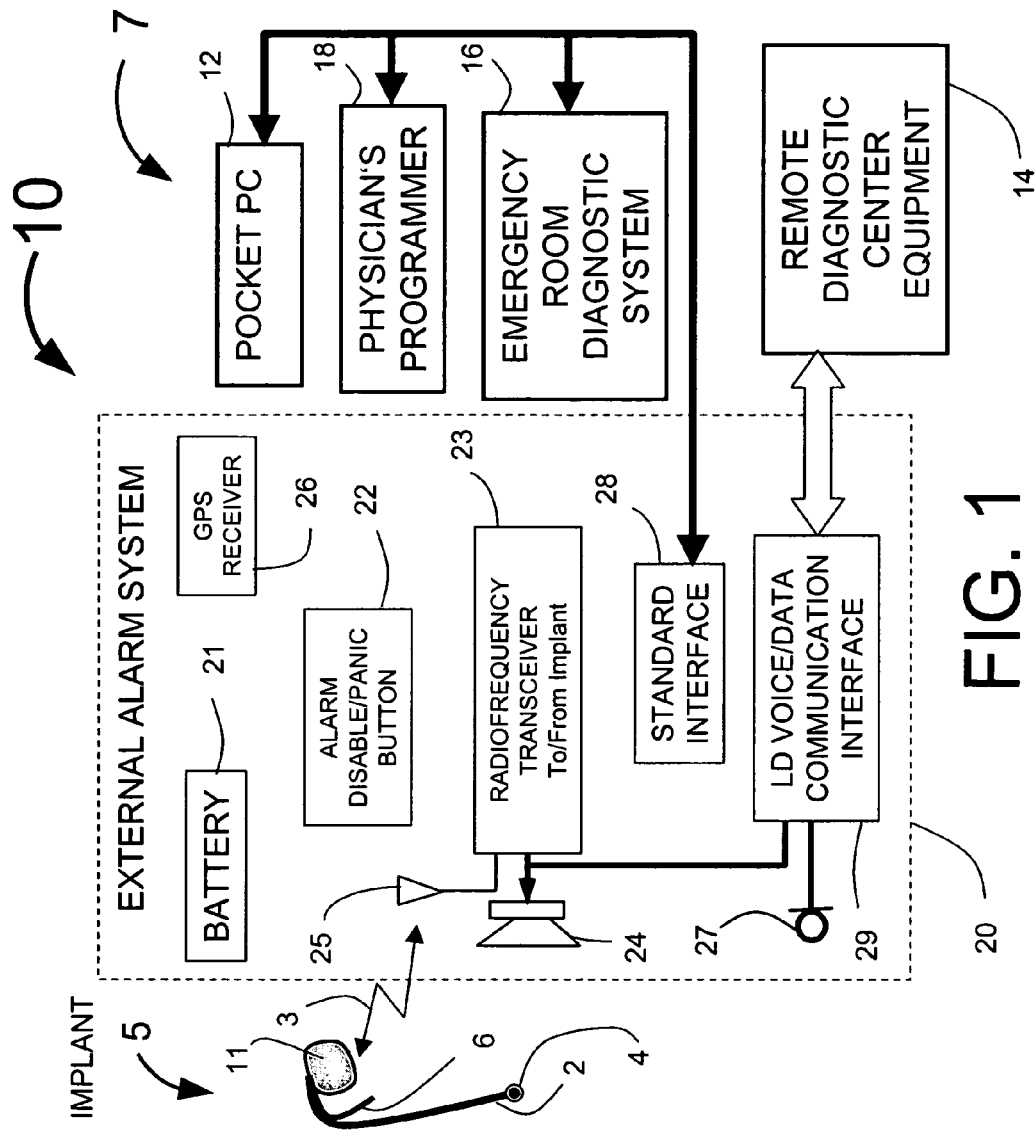
FIG. 1 illustrates a Guardian system for the detection of a cardiac event such as an ST segment shift indicative of coronary ischemia and for warning the patient that a cardiac event is occurring.

FIG. 1 illustrates one embodiment of the Guardian system 10 consisting of an implanted cardiosaver system 5 and external equipment 7. The cardiosaver system 5 includes a cardiosaver 11, an antenna 6 and an electrode 4 that is part of a lead 2. The cardiosaver 11 includes electronic circuitry that can detect a cardiac event such as an acute myocardial infarction or arrhythmia and can warn the patient when a cardiac event occurs. The cardiosaver 11 can store the patient's electrogram for later readout and can send and receive wireless signals 3 to and from the external equipment 7 via the implanted antenna 6 and the external antenna 25. The functioning of the cardiosaver system 5 will be explained in greater detail with the assistance of FIG. 2.

The cardiosaver system 5 has at least one lead 2 with at least one electrode 4. In fact, the cardiosaver system 5 could utilize as few as one lead or as many as three and each lead could have as few as one electrode or as many as eight electrodes. The lead 2 in FIG. 1 could advantageously be placed subcutaneously or through the patient's vascular system with the electrode 4 being placed into the apex of the right ventricle. For example, the lead 2 could be placed in the right ventricle or right atrium or the superior vena cava similar to the placement of leads for pacemakers and ICDs. The metal case of the cardiosaver 11 could serve as an indifferent electrode with the electrode 4 being the active electrode. Alternately, the lead 2 in FIG. 1 could be placed through the patient's vascular system with the electrode 4 being placed into the apex of the left ventricle.

The lead 2 could advantageously be placed subcutaneously at any location where the electrode 4 would provide a good electrogram signal indicative of the electrical activity of the heart. Again for the lead 2, the case of the cardiosaver 11 of the cardiosaver system 5 could be an indifferent electrode and the electrode 4 would be the active electrode. Although the Guardian system 10 described herein can readily operate with only two electrodes, or one electrode and the case of the cardiosaver being the other electrode, it is envisioned that multiple electrodes used in monopolar or bipolar configurations could be used.

FIG. 1 also shows the external equipment 7 that consists of an external alarm transceiver 20, a physician's programmer 18, a pocket PC 12, an emergency room diagnostic system 16 and the equipment 14 in a remote diagnostic center. The external equipment 7 provides the means to interact with the cardiosaver system 5. These interactions include programming the cardiosaver 11, retrieving data collected by the cardiosaver system 5, and handling alarms generated by the cardiosaver 11. It should be understood that the cardiosaver system 5 could operate with some but not all of the external equipment 7.

The external alarm transceiver 20 includes a battery 21, an alarm disable/panic button 22, a radio frequency transceiver 23, a microphone 27, an alarm-speaker 24, an antenna 25, a GPS satellite receiver 26, and a standard interface 28 for providing wired or wireless communication with the pocket PC 12, emergency room diagnostic system 16, or physician's programmer 18. A long distance voice/data communications interface 29 provides connectivity to the remote diagnostic center equipment 14 through voice and data telecommunications networks. For example, the microphone 27 and speaker 24 could be used for wired or wireless telephone calls to and from a medical practitioner at the remote diagnostic center. A built-in modem as part of the interface 29 would allow data to be transmitted to and from the remote diagnostic center equipment 14 over a voice connection. Alternately, a data communications capability of the interface 29 could allow data to be sent or received through a wired or wireless data network. The external alarm transceiver 20 may be a separate unit that can be carried by the patient and used by the patient's physician as the data interface to the cardiosaver system 5 or it may also be built into the pocket PC 12, physician's programmer 18 or emergency room diagnostic system 16

The pocket PC also described by Fischell et al. in U.S. Pat. No. 6,609,023 can provide the patient or physician the ability to check the status of the cardiosaver 11 and display a limited set of electrogram data uploaded from the cardiosaver 11.

The emergency room diagnostic system 16 is a more sophisticated system that can upload and display any of the data stored within the cardiosaver 11 and would, in its preferred embodiment, use a touch screen display to facilitate triage of patients arriving in an emergency room who have the cardiosaver system 5. This should greatly reduce the time from arrival at the emergency room until treatment for cardiosaver system patients having a cardiac event.

The purpose of the physician's programmer 18 shown in FIG. 1 is to set and/or change the operating parameters of the implanted cardiosaver system 5 and to read out data stored in the memory of the cardiosaver 11 such as stored electrogram segments as described by Fischell et al. in U.S. Pat. No. 6,609,023.

The external alarm transceiver 20 would typically be a pager-sized device that the patient would carry on his person or keep in close proximity. If a cardiac event is detected by the cardiosaver system 5, an alarm message is sent by a wireless signal 3 to the alarm transceiver 20 via the antennas 6 and 25. When the alarm is received by the alarm transceiver 20, a patient alerting sound is played through the loudspeaker 24 to warn the patient that a cardiac event has occurred. Examples of such sounds include a periodic buzzing, a sequence of tones and/or a speech message that instructs the patient as to what actions should be taken. Furthermore, the alarm transceiver 20 can, depending upon the nature of the signal 3, send an outgoing message to the remote diagnostic center equipment 14 to alert medical practitioners that a cardiosaver system alarm has occurred. The medical practitioners can then utilize the voice communications capabilities of the remote diagnostic center equipment 14 to call back the patient similar to the call that occurs to car drivers through the ONSTAR service when their car's air bags deploy in an accident. The optional GPS receiver 26 would allow the data sent to the remote diagnostic center equipment 14 to include patient location to facilitate the summoning of emergency medical services.

The alarm disable/panic button 22 will turn off both the internal alarm of the implant 5 and the sound being emitted from the loudspeaker 24. If no alarm is occurring, then pressing the alarm disable/panic button 22 will place a voice and/or data call to the remote diagnostic center similar to the call that is placed when the ONSTAR button is pressed in a car equipped to access the ONSTAR service. GPS information and a subset of patient electrogram data may be sent as well to the medical practitioners at the remote diagnostic center. The remotely located medical practitioner could then analyze the electrogram data and call the patient back to offer advice as to whether there is an emergency situation or the situation could be routinely handled by the patient's personal physician at some later time.

Figure 2:
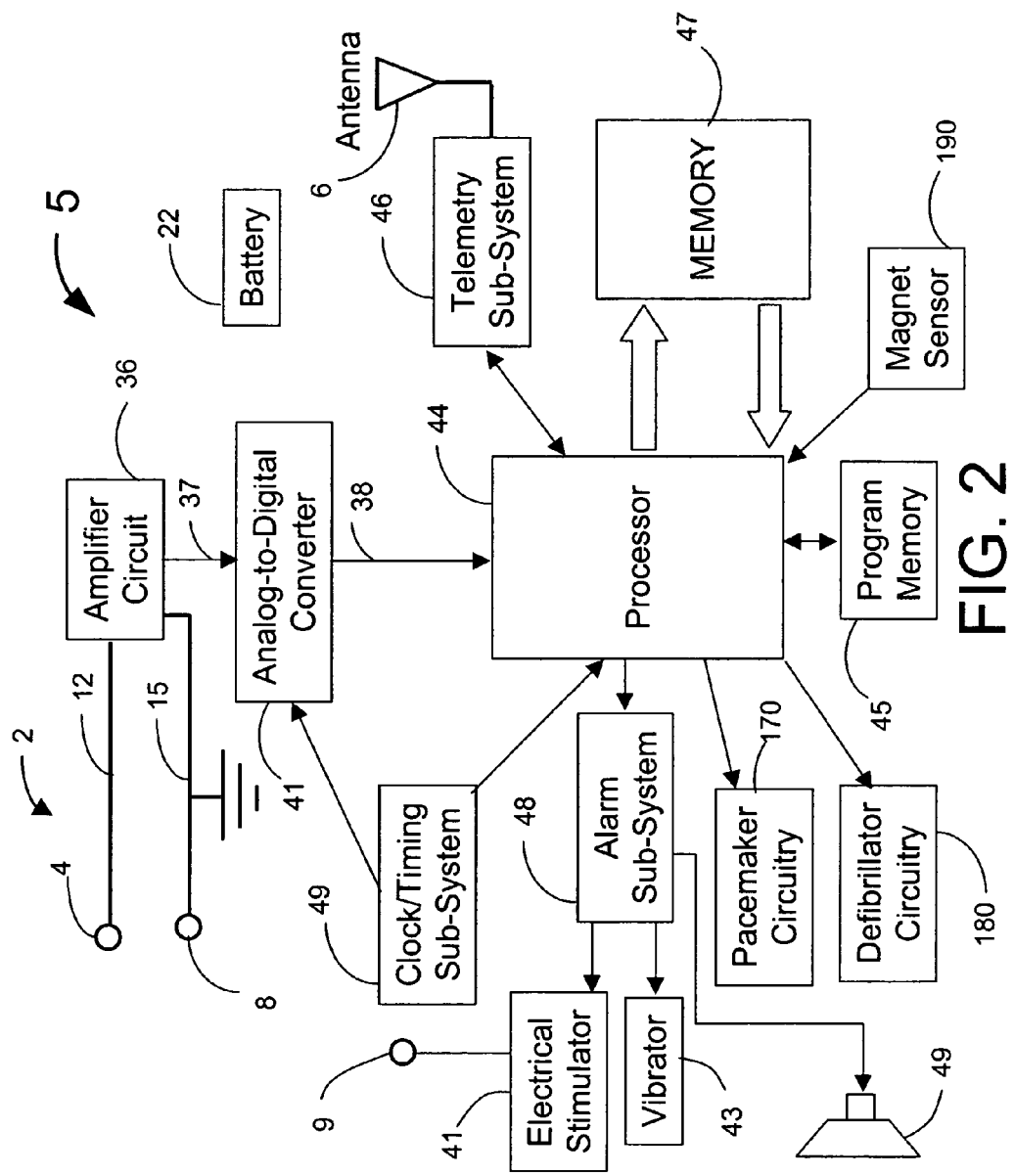
FIG. 2 is a block diagram of the implanted cardiosaver system.

FIG. 2 is a block diagram of the cardiosaver system 5. The lead 2 includes the electrode 4 and the wire 12. The wire 12 connects the electrode 4 to the amplifier circuit 36 that is also connected by the wire 15 to the cardiosaver case 8 acting as an indifferent electrode. The amplified electrogram signals 37 from the amplifier circuit 36 are converted to digital signals 38 by the analog-to-digital converter 41. The digital electrogram signals 38 are then sent to the electrical signal processor 44. The processor 44 in conjunction with the memory 47 can process the digital signals 38 according to the programming instructions stored in the program memory 45. This programming (i.e. software) enables the cardiosaver system 5 to detect the occurrence of a cardiac event such as an ST segment elevation that is indicative of an acute myocardial infarction.

A clock/timing sub-system 49 provides the means for timing specific activities of the cardiosaver system 5 including the absolute or relative time stamping of detected cardiac events. The clock/timing sub-system 49 can also facilitate power savings by causing components of the cardiosaver system 5 to go into a low power stand-by mode in between times for electrogram signal collection and processing. Such cycled power savings techniques are often used in implantable pacemakers and defibrillators. In an alternative embodiment, the clock/timing sub-system can be provided by a program subroutine run by the central processing unit 44. It is also envisioned that the processor 44 may include an integral or external First-In-First-Out (FIFO) buffer memory to allow saving of data from before the detection of a cardiac event.

Techniques for detecting cardiac events by the processor 44 are described by Fischell et al. in U.S. Pat. No. 6,609,023.

An important aspect of the present invention is the filtering of the electrical signals sensed by the electrodes 4 and 8. The preferred embodiment of the present invention cardiosaver 11 (FIG. 1) will include high pass and/or low pass filtering of the electrical signals in the amplifier circuit 36. An alternative embodiment would introduce filtering in any one, two or all of the following locations:

1. a separate analog filter between the amplifier circuit 36 and analog-to-digital converter 41,
2. a separate digital filter circuit placed between the analog-to-digital converter 41 and the processor 44, and/or
3. digital filtering performed by the processor 44 on the digital signals 38.

The memory 47 includes specific memory locations for patient data, electrogram segment data and any other relevant data.

It is envisioned that the cardiosaver system 5 could also contain pacemaker circuitry 170 and/or defibrillator circuitry 180 similar to the cardiosaver system described by Fischell, et al. et al. in U.S. Pat. No. 6,230,049.

The alarm sub-system 48 contains the circuitry and transducers to produce the internal alarm signals for the cardiosaver 11 (FIG. 1). The internal alarm signal can be a mechanical vibration, a sound or a subcutaneous electrical tickle or shock.

The telemetry sub-system 46 with antenna 6 provides the cardiosaver system 5 with the means for two-way wireless communication to and from the external equipment 7 of FIG. 1. It is also envisioned that short-range telemetry such as that typically used in pacemakers and defibrillators could also be applied to the cardiosaver system 5. It is also envisioned that standard wireless protocols such as Bluetooth and 802.11a or 802.11b might be used to provide communication with a wider group of peripheral devices.

A magnet sensor 190 may be incorporated into the cardiosaver system 5. The primary purpose for a magnet sensor 190 is to keep the cardiosaver system 5 in an off condition until it is checked out just before it is implanted into a patient. This can prevent depletion of the battery life in the period between the time that the cardiosaver system 5 is packaged at the factory and the day it is implanted.

The preferred embodiment of the present invention associated with a pacemaker/ICD or combined pacemaker/ICD would have the event detection and alerting function integrated within the pacemaker, ICD or combined pacemaker/ICD. It is also envisioned that the lead might connect both to a standard pacemaker, ICD or combined pacemaker/ICD and a cardiosaver having an electrical signal processor for cardiac event detection and the ability to generate an escalating patient alert.

Figure 3:
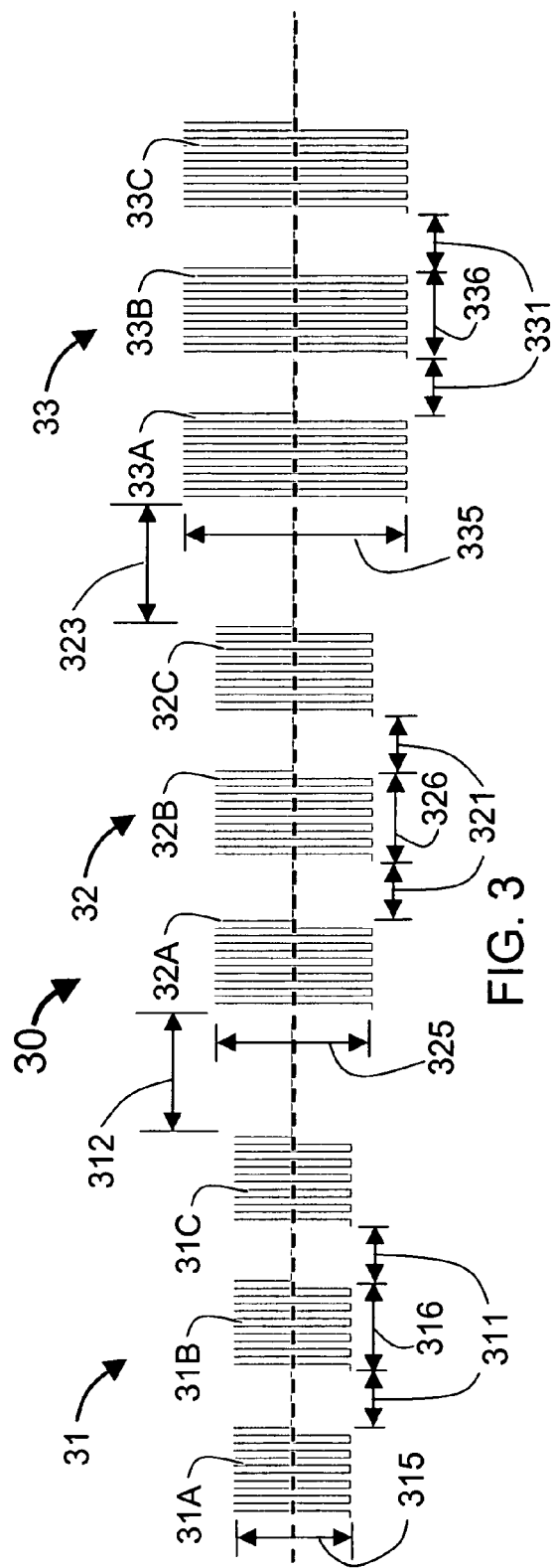
FIG. 3 illustrates an increase in amplitude of an alarm signal as the patient alert escalates.

FIG. 3 is an example of use of increasing the amplitude of an alarm signal to provide an escalating patient alert. FIG. 3 shows the progression over time of the three successive sets of alerting signals 31, 32 and 33 of the alarm signal 30. The pattern displayed in FIG. 3 can be applied to internal and/or external alarm signals using vibration, sound, electrical stimulation (tickle) or a visual display. The set 31 has alerting signals 31A, 31B and 31C, each alerting signal within the set 31 having an amplitude 315, a duration 316, and a time interval between the alerting signals 31A and 31B and the alerting signals 31B and 31C of 311. The set 32 has alerting signals 32A, 32B and 32C, each alerting signal within the set 32 having an amplitude 325, a duration 326 and a time interval between the alerting signals 32A and 32B and the alerting signals 32B and 32C of 321. The set 33 has alerting signals 33A, 33B and 33C, each alerting signal within the set 33 having an amplitude 335, a duration 336 and a time interval between the alerting signals 33A and 33B and the alerting signals 33B and 33C of 331. The time interval between the sets 31 and 32 is 312 and the time interval between the sets 32 and 33 is 323. It can be seen that the alarm signal 30 provides an escalating patient alert by progressively increasing the amplitude over time as the amplitude 335 is greater than the amplitude 325 which is greater than the amplitude 315. Ideally, such an escalating amplitude alert would start at level barely detectable by the patient and increase to a level that cannot be ignored. The physician's programmer 18 of FIG. 1 would typically provide the capability to test different patterns and intensities of both internal and external alarm signals with the patient to set a patient alert that cannot be missed while also reducing the potential to startle the patient. It is also envisioned that the amplitude might also increase for successive alerting signals within a set. The present invention includes any increase in amplitude over time in any type of internal or external alarm signal. It is also envisioned that after a preset escalation period, the amplitude would reach a pre-set level and no longer increase. An important feature of the programmer 18 would be to set the initial alerting signal amplitude so that it is just barely perceptible and to set the highest alerting signal amplitude at a level that cannot be missed. Although FIG. 3 shows a constant duration of the alerting signals (316, 326 and 336), a constant time between sets (312 and 323) and constant times between alerting signals within a set (311, 321 and 331) they need not be constant. The times between alerting signals 311, 321 and 322 are typically less than one second while the times between sets 312 and 323 are typically greater than one second.

Figure 4:
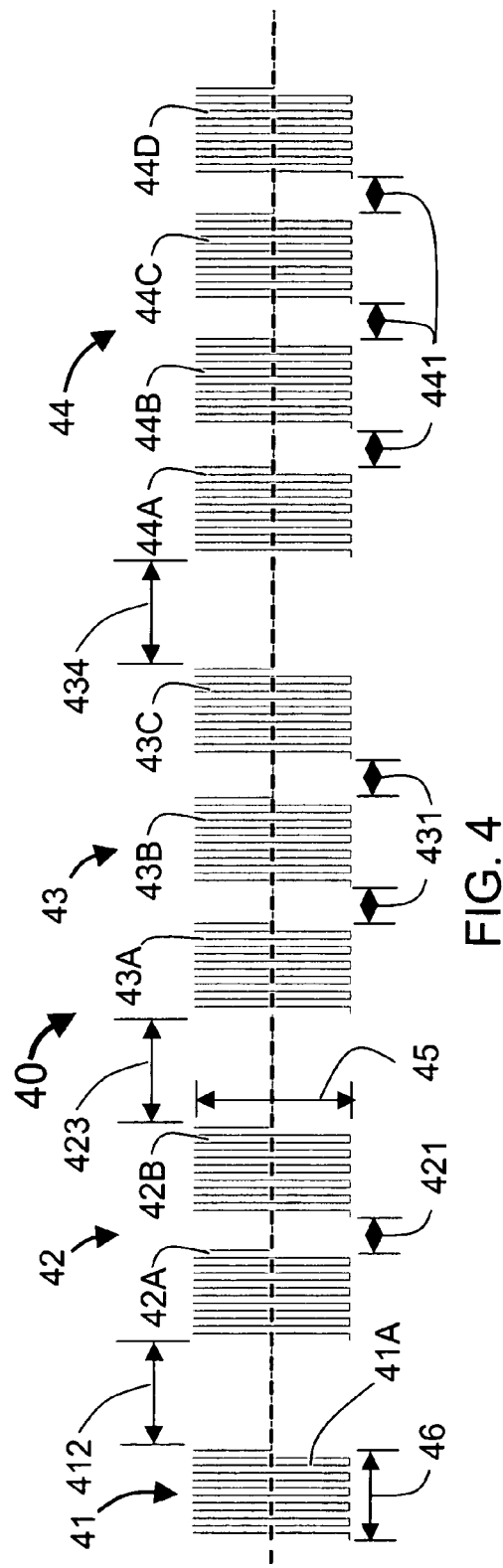
FIG. 4 illustrates a change in the number of alerting signals per set as the patient alert escalates.

FIG. 4 is an example of use of increasing number of alerting signals within each set of alerting signals of an alarm signal to provide an escalating patient alert. FIG. 4 shows the progression over time of the four successive sets of alerting signals 41, 42, 43 and 44 of the alarm signal 40. The pattern displayed in FIG. 4 can be applied to internal and/or external alarm signals using vibration, sound, electrical stimulation (tickle) or a visual display. The set 41 has one alerting signal 41A, the alerting signal 41A having an amplitude 45 and a duration 46. The set 42 has two alerting signals 42A and 42B, each alerting signal within the set 42 having an amplitude 45, a duration 46 and a time interval between the alerting signals 42A and 42B of 421. The set 43 has three alerting signals 43A, 43B and 43C, each alerting signal within the set 43 having an amplitude 45, a duration 46 and a time interval between the alerting signals 43A and 43B and the alerting signals 43B and 43C of 431. The set 44 has four alerting signals 44A, 44B, 44C and 44D, each alerting signal within the set 44 having an amplitude 45, a duration 46, and a time interval between the alerting signals 44A and 44B, the alerting signals 44B and 44C, and the alerting signals 44C and 44D of 44. The time interval between the sets 41 and 42 is 412, the time interval between the sets 42 and 43 is 423, the time interval between the sets 43 and 44 is 434. It can be seen that the alarm signal 40 provides an escalating patient alert by progressively increasing the number of alerting signals per set over time.

Although the pattern shown in FIG. 4 shows an increase by one of the number of alerting signals in successive sets, it is envisioned that an increase in the number of alerting signals per set could occur faster, e.g. an increase by two from one set to the next. It is also envisioned that the increase in the number of alerting signals per set could occur more slowly, e.g. an increase by one after every two sets. Ideally, such an escalating alert would start with a single alerting signal in a set such as the set 41 and increase to a preset number of alerting signals per set. The present invention includes any progressive increase in the number of alerting signals per set in an internal or external alarm signal. It is also envisioned that after a preset escalation period, the number of alerting signals per set would reach a pre-set level and no longer increase. Although FIG. 4 shows a constant amplitude 45, a constant duration of the alerting signals 46, a constant time between sets (412, 423 and 434) and constant times between alerting signals within a set (421, 431 and 441), they need not be constant. The times between alerting signals 421, 431 and 441 are typically less than one second while the times between sets 412, 423 and 434 are typically greater than one second. It is also envisioned that as the number of alerting signals within a set increases, the duration 46 of the alerting signals might decrease. This will subsequently reduce the total time for sets of alerting signals as the number of alerting signals increases.

Figure 5:
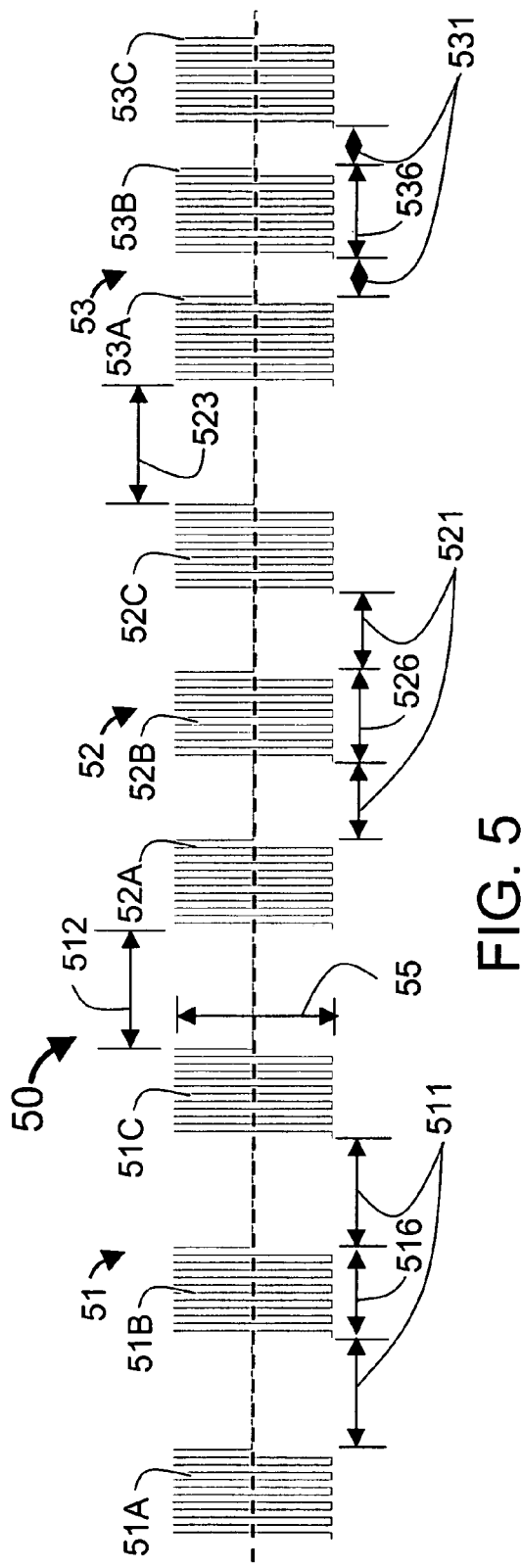
FIG. 5 illustrates a decrease in the time between alerting signals within a set of alerting signals as the patient alert escalates.

FIG. 5 is an example of use of decreasing time between alerting signals within a set of alerting signals of an alarm signal to provide an escalating patient alert. FIG. 5 shows the progression over time of the three successive sets of alerting signals 51, 52 and 53 of the alarm signal 50. The pattern displayed in FIG. 5 can be applied to internal and/or external alarm signals using vibration, sound, electrical stimulation (tickle) or a visual display. The set 51 has alerting signals 51A, 51B and 51C, each alerting signal within the set 51 having an amplitude 55, a duration 516 and a time interval between the alerting signals 51A and 51B and the alerting signals 51B and 51C of 511. The set 52 has alerting signals 52A, 52B and 52C, each alerting signal within the set 52 having an amplitude 55, a duration 526 and a time interval between the alerting signals 52A and 52B and the alerting signals 52B and 52C of 521. The set 53 has alerting signals 53A, 53B and 53C, each alerting signal within the set 53 having an amplitude 55, a duration 536 and a time interval between the alerting signals 53A and 53B and the alerting signals 53B and 53C of 531. The time interval between the sets 51 and 52 is 512 and, the time interval between the sets 52 and 53 is 523. It can be seen that the alarm signal 50 provides an escalating patient alert by progressively decreasing the time between alerting signals within successive sets over time as the time 511 is greater than the time 521 which is greater than the time 531. It is also envisioned that the time between alerting signals might decrease for successive alerting signals within a set. The present invention includes any progressive decrease in the time between successive alerting signals in an internal or external alarm signal. It is also envisioned that after a preset escalation period, the time between alerting signals would reach a pre-set level and no longer decrease. Although FIG. 5 shows a constant amplitude 55, a constant duration of the alerting signals (516, 526 and 536) and a constant time between sets (512 and 523) they need not be constant. The times between alerting signals 511, 521 and 531 are typically less than the times between sets 512 and 523.

Figure 6:
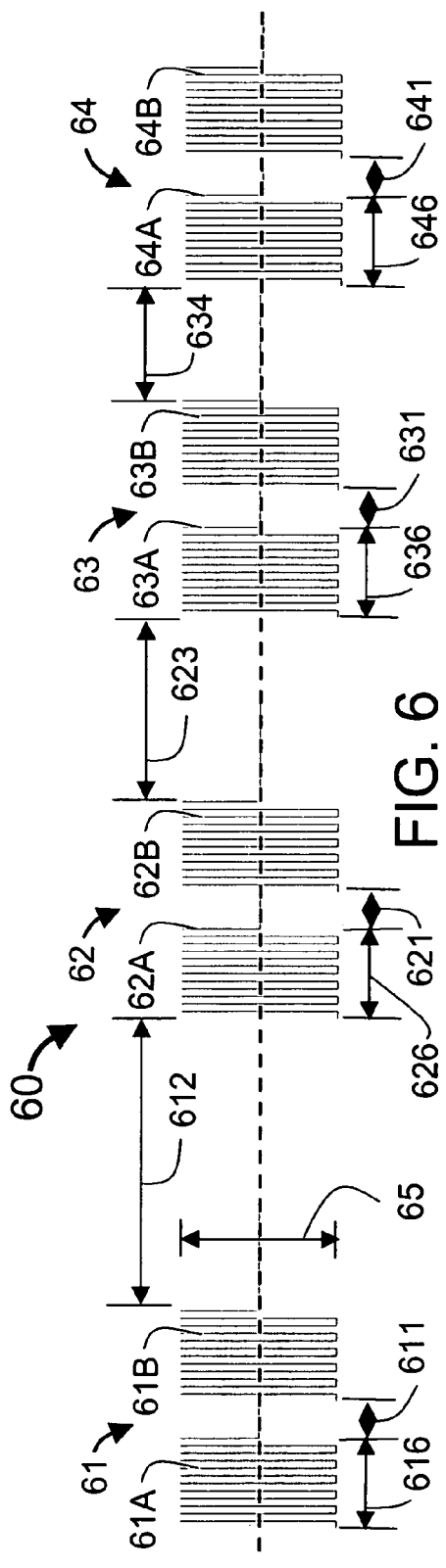
FIG. 6 illustrates a decrease in the time between sets of alerting signals as the patient alert escalates.

FIG. 6 is an example of use of decreasing time between sets of alerting signals of an alarm signal to provide an escalating patient alert. FIG. 6 shows the progression over time of the four successive sets of alerting signals 61, 62, 63 and 64 of the alarm signal 60. The pattern displayed in FIG. 6 can be applied to internal and/or external alarm signals using vibration, sound, electrical stimulation (tickle) or a visual display. The set 61 has alerting signals 61A and 61B, each alerting signal within the set 61 having an amplitude 65, a duration 616 and a time interval between the alerting signals 61A and 61B of 611. The set 62 has alerting signals 62A and 62B, each alerting signal within the set 62 having an amplitude 65, a duration 626 and a time interval between the alerting signals 62A and 62B of 621. The set 63 has alerting signals 63A and 63B, each alerting signal within the set 63 having an amplitude 65, a duration 636 and a time interval between the alerting signals 63A and 63B of 631. The set 64 has alerting signals 64A and 64B, each alerting signal within the set 64 having an amplitude 65, a duration 646 and a time interval between the alerting signals 64A and 64B of 641. The time interval between the sets 61 and 62 is 612, the time interval between the sets 62 and 63 is 623 and the time interval between the sets 63 and 64 is 634. It can be seen that the alarm signal 60 provides an escalating patient alert by progressively decreasing the time between sets of alerting signals over time as the time 612 is greater than the time 623 which is greater than the time 634. The present invention includes any progressive decrease in the time between successive sets of alerting signals in an internal or external alarm signal. It is also envisioned that after a preset escalation period, the time between sets of alerting signals would reach a pre-set level and no longer decrease. Although FIG. 6 shows a constant amplitude 65, a constant duration of the alerting signals (616, 626, 636 and 646) and a constant time between alerting signals within each set (611, 621, 631 and 641), they need not be constant. The times between alerting signals 611, 621, 631 and 641 are typically less than the times between sets 612,623 and 634.

FIG. 7 is an example of use of increasing frequency (decrease in wavelength) for successive sets of alerting signals of an alarm signal to provide an escalating patient alert. FIG. 7 shows the progression over time of the three successive sets of alerting signals 71, 72 and 73 of the alarm signal 70. The pattern displayed in FIG. 7 can be applied to internal and/or external alarm signals using vibration, sound, electrical stimulation (tickle) or a visual display. For a visual display a change in frequency would typically entail a change in color. The set 71 has alerting signals 71A and 71B, each alerting signal within the set 71 having a wavelength 717, an amplitude 75, a duration 716 and a time interval between the alerting signals 71A and 71B of 711. The set 72 has alerting signals 72A and 72B, each alerting signal within the set 72 having a wavelength 727, an amplitude 75, a duration 726 and a time interval between the alerting signals 72A and 72B of 721. The set 73 has alerting signals 73A and 73B, each alerting signal within the set 73 having a wavelength 737, an amplitude 75, a duration 736 and a time interval between the signals 73A and 73B of 731. The time interval between the sets 71 and 72 is 712 and the time interval between the sets 72 and 73 is 723. It can be seen that the alarm signal 70 provides an escalating patient alert by progressively decreasing the wavelength (increasing the frequency) of the alerting signals within successive sets over time as the wavelength 717 is greater than the wavelength 727 which is greater than the wavelength 737. It is also envisioned that the wavelength of the alerting signals might progressively decrease for successive alerting signals within a set. The present invention includes any use of a progressive decrease in the wavelength (which is equivalent to an increase in frequency) of alerting signals in an internal or external alarm signal. It is also envisioned that after a preset escalation period, the frequency of the alerting signals would reach a pre-set level and no longer change. Although FIG. 7 shows a constant amplitude 75, a constant duration of the alerting signals (716, 726 and 736), a constant time between alerting signals within each set (711, 721, and 731) and a constant time between sets (712 and 723), they need not be constant. The times between alerting signals 711, 721 and 731 are typically less than the times between sets 712 and 723. Although the alerting signals 71A, 71B, 72A, 72B, 73A and 73B as well as all of the alerting signals for FIGS. 2 through 6 are shown as square waves, it is envisioned that any wave structure including sine waves and triangular waves could be used by the cardiosaver system 5 of FIG. 1.

FIG. 8 is an example of use of progressively increasing the duration of the alerting signals for successive sets of alerting signals of an alarm signal to provide an escalating patient alert. FIG. 8 shows the progression over time of the three successive sets of alerting signals 81, 82 and 83 of the alarm signal 80. The pattern displayed in FIG. 8 can be applied to internal and/or external alarm signals using vibration, sound, electrical stimulation (tickle) or a visual display. The set 81 has alerting signals 81A and 81B, each alerting signal within the set 81 having an amplitude 85, a duration 816 and a time interval between the alerting signals 81A and 81B of 811. The set 82 has alerting signals 82A and 82B, each alerting signal within the set 82 having an amplitude 85, a duration 826 and a time interval between the alerting signals 82A and 82B of 821. The set 83 has alerting signals 83A and 83B each alerting signal within the set 83 having an amplitude 85, a duration 836 and a time interval between the alerting signals 83A and 83B of 831. The time interval between the sets 81 and 82 is 812 and the time interval between the sets 82 and 83 is 823. It can be seen that the alarm signal 80 provides an escalating patient alert by progressively increasing the duration of the alerting signals for successive sets over time as the duration 836 is greater than the duration 826 which is greater than the duration 816. It is also envisioned that the duration of alerting signals might increase for successive alerting signals within a set. The present invention includes any progressive increase in the duration of alerting signals in an internal or external alarm signal. It is also envisioned that after a preset escalation period, the duration of the alerting signals would reach a pre-set level and no longer increase. Although FIG. 8 shows a constant amplitude 85, a constant time between alerting signals within each set (811, 821 and 831) and a constant time between sets (812 and 823) they need not be constant. The times between alerting signals 811, 821 and 831 are typically less than the times between sets 812 and 823.

Figure 9:
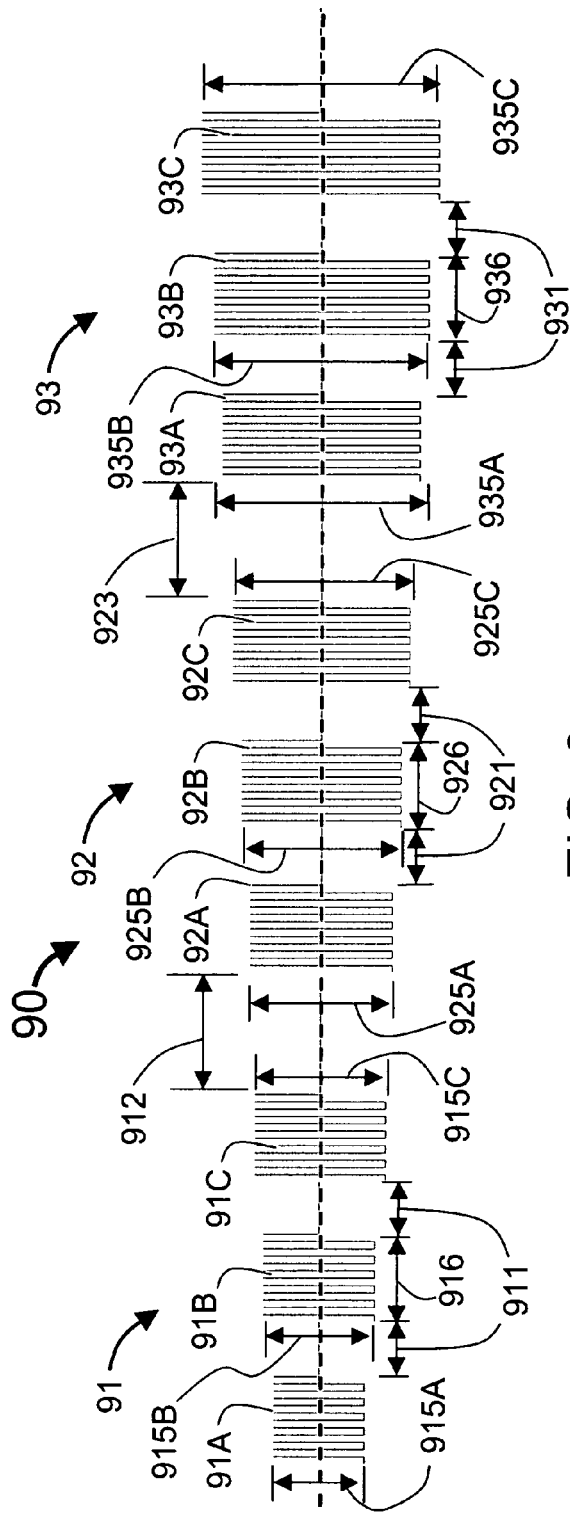
FIG. 9 illustrates a progressive increase in the alerting signals within each set of alerting signals of an alarm signal; and, FIG. 10 illustrates an escalating patient alert with increasing intensity, increasing number of alerting signals per set, decreasing time between alerting signals within a set and decreasing time between sets of alerting signals.

FIG. 9 is an alternative to the alarm signal 30 of FIG. 3 as an example of use of increasing amplitude of an alarm signal to provide an escalating patient alert. FIG. 9 shows the progression over time of the three successive sets of alerting signals 91, 92 and 93 of the alarm signal 90. The pattern displayed in FIG. 9 can be applied to internal and/or external alarm signals using vibration, sound, electrical stimulation (tickle) or a visual display. The set 91 has alerting signals 91A, 91B and 91C with amplitudes 915A, 915B and 915C respectively. Each alerting signal within the set 91 has a duration 916 and a time interval between the alerting signals 91A and 91B and the alerting signals 91B and 91C of 911. The set 92 has alerting signals 92A, 92B and 92C with amplitudes 925A, 925B and 925C respectively. Each alerting signal within the set 92 has a duration 926 and a time interval between the alerting signals 92A and 92B and the alerting signals 92B and 92C of 921. The set 93 has alerting signals 93A, 93B and 93C with amplitudes 935A, 935B and 935C respectively. Each alerting signal within the set 93 has a duration 936 and a time interval between the alerting signals 93A and 93B and the alerting signals 93B and 93C of 931. The time interval between the sets 91 and 92 is 912 and the time interval between the sets 92 and 93 is 923. It can be seen that the alarm signal 90 provides an escalating patient alert by progressively increasing the amplitude over time as the amplitude increases with each successive alerting signal within each set, e.g. 915C is greater than the amplitude 915B which is greater than the amplitude 915A. There is also shown a progressive increase in amplitude between sets 91, 92 and 93. Ideally, such an escalating amplitude alert would start at level barely detectable by the patient and increase to a level that cannot be ignored. The physician's programmer 18 of FIG. 1 would typically provide the capability to test different patterns and intensities of both internal and external alarm signals with the patient to set a patient alert that cannot be missed while also reducing the potential to startle the patient. It is also envisioned that after a pre-set escalation period, the amplitude would reach a pre-set level and no longer increase. Although FIG. 9 shows a constant duration of the alerting signals (916, 926 and 936), a constant time between sets (912 and 923) and constant times between alerting signals within a set (911, 921 and 931) they need not be constant. The times between alerting signals 911, 921 and 931 are typically less than one second while the times between sets 912 and 923 are typically greater than one second.

Figure 10:
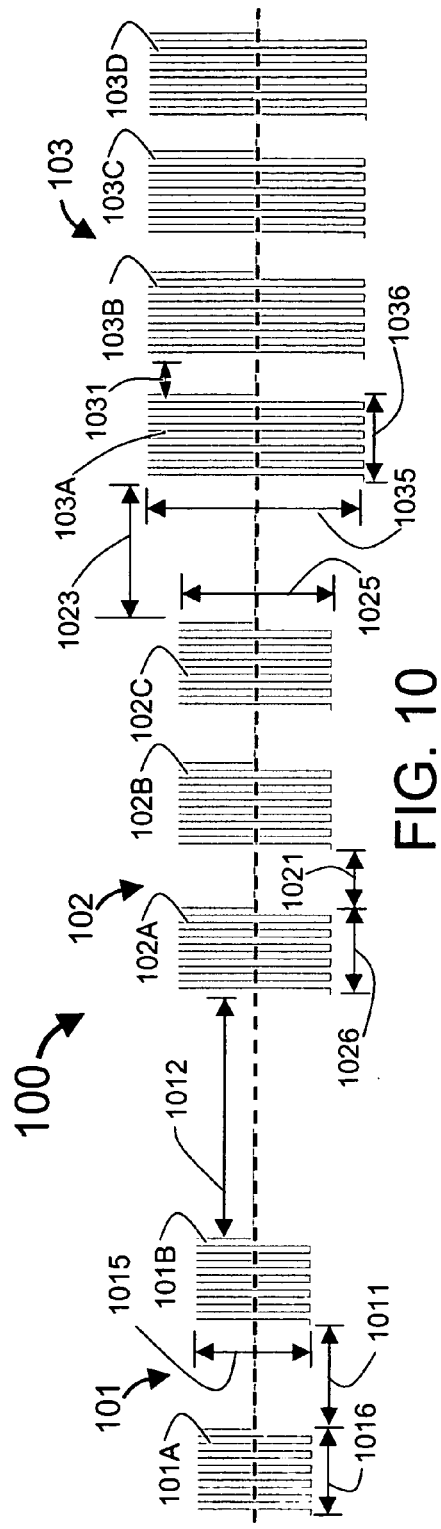

FIG. 10 is an example of use of a combination of progressive escalating features of an alarm signal to provide an escalating patient alert. FIG. 10 shows the progression over time of the three successive sets of alerting signals 101, 102 and 103 of the alarm signal 100. The pattern displayed in FIG. 10 can be applied to internal and/or external alarm signals using vibration, sound, electrical stimulation (tickle) or a visual display. The set 101 has two alerting signals 101A and 101B, each alerting signal within the set 101 having an amplitude 1015, a duration 1016 and a time interval between the alerting signals 101A and 1011B of 1011. The set 102 has three alerting signals 102A, 102B and 102C, each alerting signal within the set 102 having an amplitude 1025, a duration 1026 and a time interval between the alerting signals 102A and 102B and the alerting signals 102B and 102C of 1021. The set 103 has four alerting signals 103A, 103B, 103C and 103D, each alerting signal within the set 103 having an amplitude 1035, a duration 1036 and a time interval between the alerting signals 103A and 103B, the alerting signals 103B and 103C and the alerting signals 103C and 103D of 1031. The time interval between the sets 101 and 102 is 1012 and the time interval between the sets 102 and 103 is 1023. It can be seen that the alarm signal 100 provides an escalating patient alert by combining several of the escalating features seen in FIGS. 3 though 7 including:

a) progressively increasing the amplitude of the alerting signals over time as the amplitude 1035 is greater than the amplitude 1025 which is greater than the amplitude 1015;
b) progressively increasing the number of alerting signals in each set as the set 101 contains two alerting signals, the set 102 contains 3 alerting signals and the set 103 contains 4 alerting signals;
c) progressively decreasing the time interval between alerting signals within each set as the time interval 1011 is greater than the time interval 1021 which is greater than the time interval 1031; and,
d) progressively decreasing the time interval between sets of alerting signals as the time interval 1012 is greater than the time interval 1023, Although the alarm signal 100 shows a combination of four different escalation features of the alarm signals 30, 40, 50 and 60, it is envisioned that an escalating signal could include any combination of two, three or more of the escalation techniques shown in the examples of FIGS. 3 through 10. It is also envisioned that the present invention would also include any escalating alerting pattern that would over time become more and more perceptible to a patient.

Although the techniques for escalating patient alerting has been discussed with respect to an implanted system for the detection of cardiac events, it is also envisioned that these techniques are equally applicable to systems for the detection of cardiac events that are entirely external to the patient. For clarity, the time interval between alerting signals within a set is hereby termed as the intra-set time interval and the time interval between sets of alerting signals is hereby termed the inter-set time interval.

Various other modifications, adaptations, and alternative designs are of course possible in light of the above teachings. Therefore, it should be understood at this time that, within the scope of the appended claims, the invention can be practiced otherwise than as specifically described herein.

What is claimed is:

1. A system for detection of cardiac events occurring in a human patient, comprising:
   (a) at least two electrodes for obtaining an electrical signal from a patient's heart;
   (b) an electrical signal processor electrically coupled to said electrodes for processing the electrical signal; and,
   (c) patient alarm means coupled to the electrical signal processor for generating a sensory alarm signal received by the patient over a predetermined time period subsequent to the electrical signal processor detecting a cardiac event, the alarm signal includes a multiplicity of successive sets of alerting signals, each set including two or more alerting signals, the alerting signals within each set being spaced apart in time by an intra-set time interval, the alarm signal escalating in sensory stimulation by decreasing the intra-set time interval in successive sets of alerting signals during the predetermined time period.

2. The system for detection of cardiac events occurring in a human patient as recited in claim 1 wherein the cardiac event is coronary ischemia indicated by a change in the ST segment of the electrical signal.

3. The system for detection of cardiac events occurring in a human patient as recited in claim 1 wherein the cardiac event is coronary ischemia indicated by a change in the ST segment of the electrical signal at an elevated heart rate.

4. The system for detection of cardiac events occurring in a human patient as recited in claim 1 wherein the cardiac event is an arrhythmia.

5. The system for detection of cardiac events occurring in a human patient as recited in claim 4 wherein the arrhythmia is high heart rate.

6. The system for detection of cardiac events occurring in a human patient as recited in claim 4 wherein the arrhythmia is low heart rate.

7. The system for detection of cardiac events occurring in a human patient as recited in claim 4 wherein the arrhythmia is an unsteady heart rate.

8. The system for detection of cardiac events occurring in a human patient as recited in claim 7 wherein the unsteady heart rate is the result of PVCs.

9. The system for detection of cardiac events occurring in a human patient as recited in claim 7 wherein the unsteady heart rate is the result of atrial fibrillation.

10. The system for detection of cardiac events occurring in a human patient as recited in claim 1 wherein the sets of two or more alerting signals are spaced apart in time by an inter-set time interval.

11. The system for detection of cardiac events occurring in a human patient as recited in claim 10 wherein the inter-set time interval is longer than the intra-set time interval.

12. The system for detection of cardiac events occurring in a human patient as recited in claim 10 wherein the inter-set time interval is greater than one second.

13. The system for detection of cardiac events occurring in a human patient as recited in claim 11 wherein the intra-set time interval is less than 1 second.

14. The system for detection of cardiac events occurring in a human patient as recited in claim 1 wherein the patient alarm means includes an internal alarm transducer disposed in an implanted medical device for output of the alarm signal internal to the patient.

15. The system for detection of cardiac events occurring in a human patient as recited in claim 14 wherein the internal alarm signal includes a vibration.

16. The system for detection of cardiac events occurring in a human patient as recited in claim 14 wherein the internal alarm signal includes a sound.

17. The system for detection of cardiac events occurring in a human patient as recited in claim 14 further including an escalating external alarm signal.

18. The system for detection of cardiac events occurring in a human patient as recited in claim 14 further including an external alarm system for generating an external alarm signal, the external alarm signal being of a constant level of sensory stimulation.

19. The system for detection of cardiac events occurring in a human patient as recited in claim 1 wherein the patient alarm means includes an external alarm system for generating the alarm signal external to the patient.

20. The system for detection of cardiac events occurring in a human patient as recited in claim 19 wherein the external alarm signal includes a vibration.

21. The system for detection of cardiac events occurring in a human patient as recited in claim 19 wherein the external alarm signal includes a visual display.

22. The system for detection of cardiac events occurring in a human patient as recited in claim 19 wherein the external alarm signal includes a sound.

23. The system for detection of cardiac events occurring in a human patient as recited in claim 19 further including an internal alarm signal transducer disposed in an implanted medical device for output of an alarm signal internal to the patient, the internal alarm signal being of a constant level of sensory stimulation.

24. The system for detection of cardiac events occurring in a human patient as recited in claim 23 wherein the external alarm signal is initiated at a preset time before the initiation of the internal alarm signal.

25. A system for detection of cardiac events occurring in a human patient, comprising:
(a) at least two electrodes for obtaining an electrical signal from a patient's heart;
(b) an electrical signal processor electrically coupled to said electrodes for processing the electrical signal; and,
(c) patient alarm means coupled to the electrical signal processor for generating a sensory alarm signal received by the patient over a predetermined time period subsequent to the electrical signal processor detecting a cardiac event, the alarm signal including a multiplicity of successive sets of alerting signals, the sets being spaced apart in time by an inter-set time interval, the alarm signal escalating in sensory stimulation by a progressively decreasing inter-set time interval being inserted between successive sets of alerting signals.

26. A The system for detection of cardiac events occurring in a human patient, comprising:
(a) at least two electrodes for obtaining an electrical signal from a patient's heart;
(b) an electrical signal processor electrically coupled to said electrodes for processing the electrical signal; and,
(c) patient alarm means coupled to the electrical signal processor for generating a sensory alarm signal received by the patient over a predetermined time period subsequent to the electrical signal processor detecting a cardiac event, the alarm signal including a multiplicity of successive sets of alerting signals, each set including one or more alerting signals, the alarm signal escalating in sensory stimulation by the number of alerting signals in each set increasing over time.

27. A system for detection of cardiac events occurring in a human patient, comprising:
(a) at least two electrodes for obtaining an electrical signal from a patient's heart;
(b) an electrical signal processor electrically coupled to said electrodes for processing the electrical signal; and,
(c) patient alarm means coupled to the electrical signal processor for generating an escalating sensory alarm signal received by the patient over a predetermined time period subsequent to the electrical signal processor detecting a cardiac event, the alarm signal including a multiplicity of successive sets of alerting signals, each set including two or more alerting signals, the alarm signal escalating in sensory stimulation by the number of alerting signals in each set increasing over time and the time interval between alerting signals in the sets of alerting signals progressively decreasing over time.

28. A system for detection of cardiac events occurring in a human patient, comprising:
(a) at least two electrodes for obtaining an electrical signal from a patient's heart;
(b) an electrical signal processor electrically coupled to said electrodes for processing the electrical signal; and,
(c) patient alarm means coupled to the electrical signal processor for generating a sensory alarm signal received by the patient over a predetermined time period subsequent to the electrical signal processor detecting a cardiac event, the alarm signal including a multiplicity of alerting signals, the alarm signal escalating in sensory stimulation by the alerting signals increasing in duration over time.

29. A system for detection of cardiac events occurring in a human patient, comprising:
   (a) at least two electrodes for obtaining an electrical signal from a patient's heart;
   (b) an electrical signal processor electrically coupled to said electrodes for processing the electrical signal; and,
   (c) patient alarm means coupled to the electrical signal processor for generating a sensory alarm signal received by the patient over a predetermined time period subsequent to the electrical signal processor detecting a cardiac event, the alarm signal including a multiplicity of alerting signals, the alarm signal escalating in sensory stimulation by the alerting signals progressively increasing in frequency over time.

30. A system for detection of cardiac events occurring in a human patient, comprising:
   (a) at least two electrodes for obtaining an electrical signal from a patient's heart;
   (b) an electrical signal processor electrically coupled to said electrodes for processing the electrical signal; and,
   (c) patient alarm means coupled to the electrical signal processor for generating an escalating sensory alarm signal received by the patient over a predetermined time period subsequent to the electrical signal processor detecting a cardiac event, the escalating alarm signal includes an internal alarm signal originating from an implanted medical device, the internal alarm signal including an electrical tickle.

31. A system for detection of cardiac events occurring in a human patient, comprising:
   (a) at least two electrodes for obtaining an electrical signal from a patient's heart;
   (b) an electrical signal processor electrically coupled to said electrodes for processing the electrical signal; and
   (c) patient alarm means coupled to the electrical signal processor for generating an escalating sensory alarm signal received by the patient over a predetermined time period subsequent to the electrical signal processor detecting a cardiac event, the escalating alarm signal includes an internal alarm signal originating from an implanted medical device, the patient alarm means including an external alarm system for generating an external alarm signal, the external alarm signal being initiated at a preset time before an initiation of the internal alarm signal.

32. The system for detection of cardiac events occurring in a human patient as recited in claim 31 wherein the external alarm is an escalating alarm signal.

33. A system for detection of cardiac events occurring in a human patient, comprising:
   (a) at least two electrodes for obtaining an electrical signal from a patient's heart;
   (b) an electrical signal processor electrically coupled to said electrodes for processing the electrical signal; and,
   (c) patient alarm means coupled to the electrical signal processor for generating an escalating sensory alarm signal received by the patient over a predetermined time period subsequent to the electrical signal processor detecting a cardiac event, the escalating alarm signal includes an internal alarm signal originating from an implanted medical device, the patient alarm means including an external alarm system for generating an external alarm signal, the external alarm signal being initiated at a preset time after the initiation of the internal alarm signal.

34. The system for detection of cardiac events occurring in a human patient as recited in claim 33 wherein the external alarm signal is an escalating alarm signal.

* * * * *